United States Patent [19]

Gross et al.

[11] Patent Number: 5,305,768
[45] Date of Patent: Apr. 26, 1994

[54] DENTAL FLOSSER UNITS AND METHOD OF MAKING SAME

[75] Inventors: Joseph Gross, Moshav Mazor; Shlomo Zucker, Mihmoret, both of Israel

[73] Assignee: Product Development (ZGS) Ltd., Petah Tikva, Israel

[21] Appl. No.: 82,707

[22] Filed: Jun. 28, 1993

Related U.S. Application Data

[63] Continuation-in-part of Ser. No. 933,638, Aug. 24, 1992, abandoned.

[51] Int. Cl.[5] ............................................. A61C 15/00
[52] U.S. Cl. ..................................... 132/321; 132/329
[58] Field of Search ................. 132/321, 322, 323, 329

[56] References Cited

U.S. PATENT DOCUMENTS

| | | | |
|---|---|---|---|
| 4,006,750 | 2/1977 | Chodorow | 132/323 |
| 4,655,233 | 4/1987 | Laughlin | 132/323 |
| 4,807,752 | 2/1989 | Chodorow | 206/63.5 |
| 4,941,488 | 7/1990 | Marxer et al. | 132/323 |
| 4,986,288 | 1/1991 | Kent et al. | 132/321 |
| 5,033,488 | 7/1991 | Curtis et al. | 132/321 |
| 5,067,503 | 11/1991 | Stile | 132/324 |
| 5,113,880 | 5/1992 | Honda et al. | 132/321 |

Primary Examiner—John G. Weiss
Assistant Examiner—Cindy A. Cherichetti
Attorney, Agent, or Firm—Benjamin J. Barish

[57] ABSTRACT

A dental flosser unit for flossing teeth includes a filament of high tensile strength terminating in thickened portions at its opposite ends. In the same described embodiments, each thickened end portion includes a ferrule enclosing and crimped to the respective filament end, and a plastic body enclosing the ferrule and the respective filament end. The filament preferably includes a plurality of threads of high tensile strength coated with a low-friction material. In another described embodiment, a plastic material is injection-molded onto each end of the filament at a temperature greater than 280° C. to melt the coating and to bond directly to the threads. A further embodiment is described in which the thickened end portion is constituted of a two-part bead having complementary socket and plug formations for firmly clamping the filament.

20 Claims, 3 Drawing Sheets

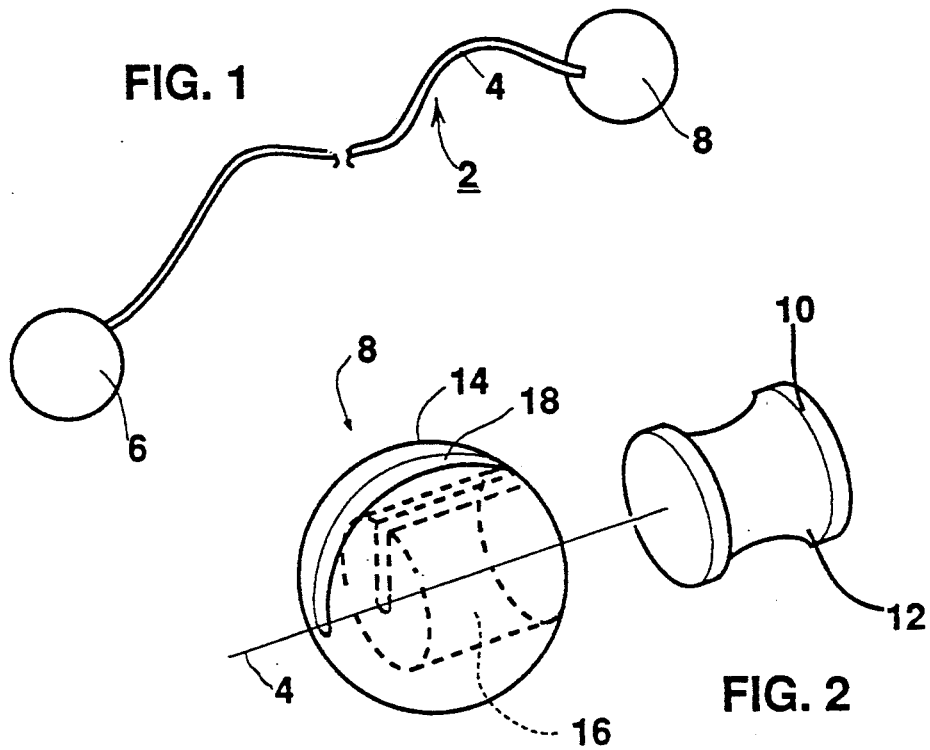
FIG. 1
FIG. 2
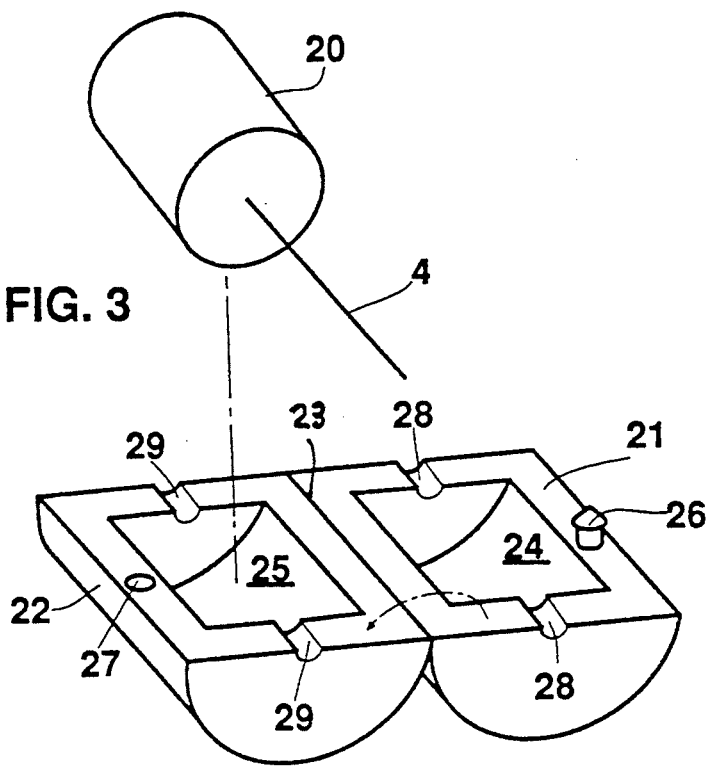
FIG. 3

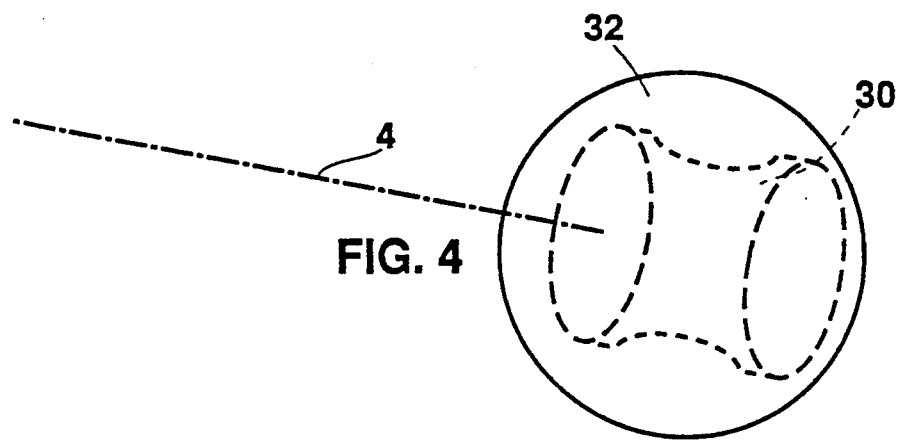
FIG. 4
FIG. 5
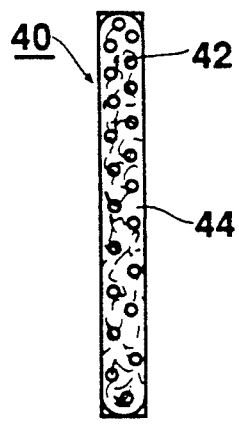
FIG. 6
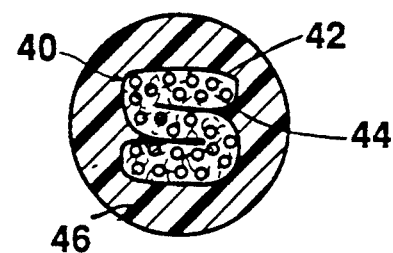

DENTAL FLOSSER UNITS AND METHOD OF MAKING SAME

RELATED APPLICATION

The present application is for a continuation-in-part of our U.S. patent application Ser. No. 07/933,638 filed Aug. 24, 1992, now abandoned.

FIELD AND BACKGROUND OF THE INVENTION

The present invention relates to dental flosser units, for cleaning the surfaces and spaces between teeth.

One type of known dental flosser unit includes a filament of high tensile strength terminating in thickened portions at its opposite ends. Various materials have been used for the filaments, including silk or plastic threads. The thickened end portions of the dental flosser unit enables the unit to be firmly held, under tension, between a pair of arms of a holder when applying the filament between the teeth to be cleaned. Considerable tensile force is thus applied to the thickened end portions, and one of the problems has been the inadequate anchoring of the thickened end portions to the filament.

It would therefore be desirable to provide a dental flosser unit in which the thickened end portions are firmly anchored to the filament under the high tensile strength applied to the end portions of the flosser unit when used for flossing teeth.

BRIEF SUMMARY OF THE INVENTION

According to one aspect of the present invention, there is provided a dental flosser unit for flossing teeth including a filament of high tensile strength terminating in thickened end portions at its opposite ends; characterized in that each of the thickened end portions includes a metal ferrule crimped to the respective filament end, and a plastic bead enclosing the ferrule and the respective filament end.

In several preferred embodiments of the invention described below, the outer plastic bead is preformed with a socket for receiving the ferrule and the respective end of the filament. In one described embodiment, the plastic bead is preformed with a slit for accommodating the filament when the ferrule crimped to the end of the filament is received within the socket. In a second described embodiment, the plastic bead is constituted of two half-sections joined together by an integral hinge permitting the two half-sections to be opened and closed, each of the half-sections being formed with a recess defining a socket for receiving the ferrule and the respective end of the filament when the two half-sections are closed.

In a third described embodiment, the plastic bead is molded over and embeds the ferrule.

In a fourth described embodiment, each of the thickened end portions includes a bead made of a first part formed with a socket for receiving the respective filament end, and a second part formed with a plug of complementary configuration as the socket for insertion into the socket of the first part, thereby firmly clamping the respective filament end therein.

According to another aspect of the present invention, there is provided a dental flosser unit for flossing teeth, comprising a filament having at least one thread of high tensile strength; a coating of low-friction material on the thread; and a plastic bead at each of the opposite ends of the filament penetrating through the coating of low-friction material and bonded directly to the at least one thread of high tensile strength.

In the preferred embodiment described below, the coating of low-friction material is a polyfluorinated hydrocarbon having a melting point of less than 280° C., and the plastic bead at each of the opposite ends of the filament has a melting point higher than 280° C.

According to a further aspect of the present invention, there is provided a method of making dental flosser unit comprising coating at least one thread of high tensile strength with a low-friction coating material having a melting point than less than 280° C.; and injection molding a plastic bead at each of the opposite ends of the thread at a temperature of at least 280° C. to melt the coating of low-friction material and to bond the plastic bead directly to the high-tensile strength thread.

According to further features in a described embodiment, the filament includes a plurality of threads of high tensile strength, each coated with a low-friction material, and all bonded together by a wax.

Further features and advantages of the invention will be apparent from the description below.

BRIEF DESCRIPTION OF THE DRAWINGS

The invention is herein described, by way of example only, with reference to the accompanying drawings, wherein:

FIG. 1 illustrates one form of dental flosser unit constructed in accordance with the present invention;

FIGS. 2, 3 and 4 illustrate three ways of producing the thickened end portion at each of the opposite ends of the dental flosser unit of FIG. 1;

FIG. 5 is an enlarged cross-sectional view illustrating a preferred construction of the filament in the dental flosser unit of FIG. 1;

FIG. 6 illustrates a further manner of producing the thickened end portion at each end of the dental flosser unit utilizing the filament of FIG. 5.

DESCRIPTION OF PREFERRED EMBODIMENTS

Figure 7:
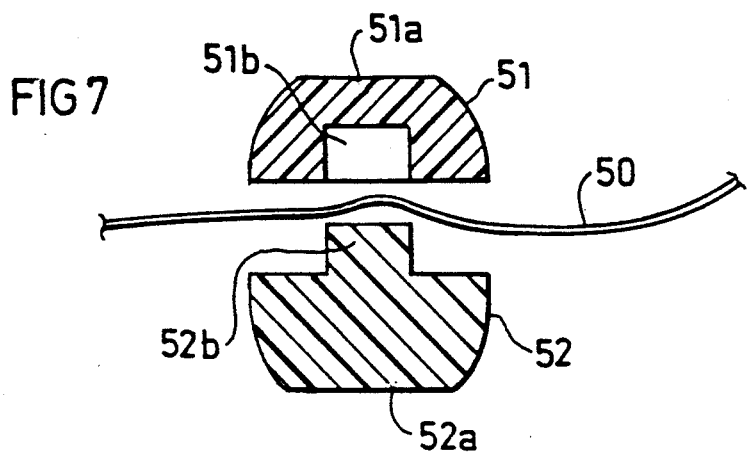
FIGS. 7-9 illustrate a fourth way of producing the thickened end portion at each of the opposite ends of the dental flosser unit of FIG. 1.

FIG. 1 illustrates one form of dental flosser unit such as now widely used for flossing teeth. This unit, generally designated 2, includes a filament 4 of high tensile strength terminating in thickened end portions 6, 8 at its opposite ends. As described earlier, such a dental flosser unit is received on a holder (not shown) having a pair of arms which receive the thickened end portions 6, 8 and apply substantial tensile force to the filament 4 as the filament is applied between the teeth to be cleaned.

FIGS. 2-4 illustrate three ways of producing the thickened end portions 6, 8 at the opposite ends of the filament 4 of FIG. 1. Although each of these figures illustrates only one thickened end portion, it will be appreciated that the opposite thickened end portion is formed in the same manner.

Thus, as shown in FIG. 2, the end of filament 4 to receive the thickened end portion 8 is first passed through a ferrule 10 open at both ends so that the ferrule encloses the respective end of the filament. The ferrule 10 is of metal, preferably aluminum, and may be of inwardly tapering diameter at its intermediate portion as shown at 12. This intermediate portion is then crimped inwardly so that the ferrule firmly grips the respective end of the filament 4.

The thickened end portion 8 of the dental flosser unit illustrated in FIG. 2 further includes a plastic bead 14 preformed with a socket 16 for receiving the ferrule 10 after the ferrule has been attached by crimping to the respective end to the filament 4. As seen in FIG. 2, socket 16 is preformed on the side of the plastic bead 14 facing its respective thickened end portion 8 (FIG. 1). Bead 14 is further preformed with a slit 18 communicating with socket 16 for accommodating the filament 4 when the ferrule 10, with the respective end of the filament secured thereto by crimping, is received within socket 16.

It will thus be seen that, in the construction illustrated in FIG. 2, ferrule 10 firmly grips the respective end of the filament 4, while the plastic bead 14 provides an enlarged surface for engagement by the respective arm of the flosser holder (not shown). This construction provides a strong mechanical bond to the thickened ends 6, 8 of the dental flosser unit 2 firmly anchoring them to the filament 4 even under the considerable tensile forces applied while using the unit for flossing between the teeth.

The construction of the thickened end portions 6, 8 illustrated in FIG. 3 also utilizes a ferrule, therein designated 20, which receives the respective end of the filament 4 and is attached thereto by crimping, as described with respect to FIG. 2. In this case, however, the outer plastic bead is constituted of two half-sections, 21, 22, joined together by an integral hinge 23 which permits the two half-sections to be opened (as shown in FIG. 3), or closed over the ferrule 20, after the ferrule has been attached by crimping to the respective end of the filament 4.

In the construction illustrated in FIG. 3, the two half-sections 21, 22 are each formed with a recess 24, 25, together defining, when the two half-sections are closed, a socket of the same cylindrical configuration as the ferrule 20. The two half-sections 21, 22 may be closed by force-fixing a pin 26 formed in half-section 21 into a blind hole 27 formed in the other half-section 22.

FIG. 3 further illustrates a pair of smaller recesses 28, 29, formed in the two half-sections 21, 22 to communicate with the recesses 24, 25, for accommodating the respective end of the filament 4 when the ferrule 20, firmly secured to the filament end, is inserted into the recesses 24, 25, and the two half-sections 21, 22 are closed. However, if the filament 4 is of sufficiently small diameter, the latter recesses 28, 29 may be omitted as the filament would be accommodated between the abutting surfaces of the two half-sections, which would thereby also more firmly anchor the plastic bead to the filament end.

While the two half-sections 21, 22 of the plastic bead illustrated in FIG. 3 are shown as of semi-cylindrical configuration, as to define a cylindrical bead when the two half-sections are closed, it will be appreciated that these half-sections could also be of semi-spherical configuration to define a spherical bead when the two half-sections are closed. Similarly, while the plastic bead 14 illustrated in FIG. 2 is of spherical configuration, it will be appreciated that it could be of cylindrical configuration, similar to FIG. 3.

FIG. 4 illustrates a further possible construction for each of the thickened end portions 6, 8 (FIG. 1) of the dental flosser unit. The construction illustrated in FIG. 4 also utilizes a ferrule 30 enclosing and crimped to the respective end of the filament 4, and a plastic body 32 enclosing the ferrule and the respective filament end. In this construction, however, the plastic body 32 is not pre-formed, as described above with respect to FIGS. 2 and 3, but rather is injection-molded over the ferrule 30 and the respective end of the filament 4 after the ferrule has been crimped to the filament end. In FIG. 4, the injection-molded plastic bead 32 is of spherical configuration, as in FIG. 2, but could also be of cylindrical configuration as in FIG. 3.

FIG. 5 illustrates a preferred construction of the filament in the dental flosser units described above. In this construction, the filament is of rectangular cross-section, as distinguished from the conventional circular configuration of filaments in flosser units. In addition, filament 40 is constituted of a plurality of threads 42 of high tensile strength each coated with a low-friction material and all held together by a microcrystalline wax 44.

In this example, the filament 40 may have a width of 0.5–3 mm and a thickness of 0.05–0.3 m, the width being from 5–20 times its thickness. The threads 42 preferably have a diameter of 0.010–0.050 mm. Particularly good results were obtained when the width was 1.0 mm, the thickness 0.1–0.2 mm, and the diameter of the threads 42 about 0.025 mm.

As examples, the threads 42 may be of nylon fibers, glass fibers, or polyester resin fibers, e.g., polyethylene terephthalate (PETP) or polybutylene terephthalate (PBTD). A preferred construction for the dental flosser unit is one which includes expanded polytetrafluoroethylene threads covered by a microcrystalline wax as described in U.S. Pat. No. 5,033,488.

When such a filament as illustrated in FIG. 5 is used in the dental flosser unit of FIG. 1, any of the constructions described above with respect to FIGS. 2–4 may be used for producing the thickened end portions 6, 8 of the flosser unit. However, FIG. 6 illustrates another construction which is particularly useful for producing the thickened end portions 6, 8 when using the filament construction of FIG. 5.

Thus, when using the filament construction of FIG. 5, the opposite ends of the filament 40 may be twisted or folded, e.g., to form an S-shape as shown in FIG. 6. A plastic material 46 is then injection-molded over the ends of the filament 40 in such manner so as to penetrate through the wax 44 and the low-friction coating on the high-tensile strength threads 42 and to become firmly bonded directly to such threads.

The low-friction coating on the threads 42 of high tensile strength is preferably a polyfluorinated hydrocarbon, e.g., Teflon (Reg.T.M.) having a melting point no higher than 280° C.; and the plastic material 46 of the end beads has a melting point higher than 280° C. and is injection-molded at a temperature higher than 280° C. Thus, the high injection temperature causes the injected plastic to melt the polyfluorinated hydrocarbon coating and thereby to directly bond to the high-tensile strength threads 42 of the filament. Particularly good results were obtained where the high-tensile strength threads 42 and the plastic material 46 were both of nylon, such as nylon 66, and the plastic material 46 was injection-molded to the ends of the filament at a temperature greater than 280° C.

Figure 8:
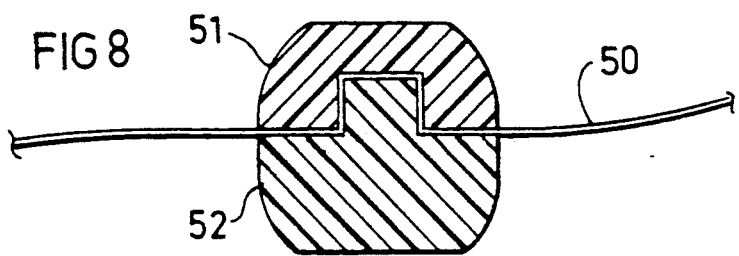
Figure 9:
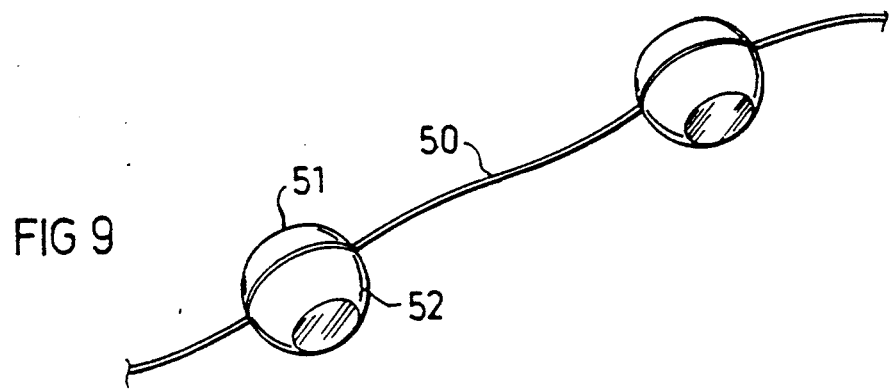

FIGS. 7–9 illustrate a further manner of providing thickened end portions at the opposite ends of the flosser filament, shown at 50. In the construction illustrated in FIGS. 7–9, each of the thickened end portions of the dental flosser unit includes a bead made of two parts 51, 52 each having an outer semi-spherical configuration but formed with flattened ends 51a, 52a. Part 51 is formed on its inner surface with a socket 51b of cylindrical configuration, and part 52 is formed on its inner surface with a plug 52b of complementary cylindrical configuration so as to be firmly received within socket 51b of part 51.

As shown in FIG. 8, the respective end of filament 50 is applied between plug 52b of part 52 and socket 51b of part 51, and the plug is then firmly inserted into the socket, thereby clamping the respective end of the filament to the two parts, as shown in FIG. 9.

The two parts are preferably made of plastic material, such as nylon, polyethylene, polyvinylchloride, etc. These parts, however, may also be made of metal, such as aluminum or copper. The two parts are preferably held together by a friction fit, but if desired an adhesive may also be used for this purpose.

While the invention has been described with respect to several preferred embodiments, it will be appreciated that these are set forth purely for purposes of example, and that many other variations, modifications and applications of the invention may be made.

What is claimed is:

1. A dental flosser unit for flossing teeth including a filament of high tensile strength terminating in thickened end portions at its opposite ends; characterized in that each of said thickened end portions includes a metal ferrule crimped to the respective filament end, and a plastic bead enclosing said ferrule and the respective filament end.

2. The dental flosser unit according to claim 1, wherein said plastic bead is preformed with a socket for receiving said ferrule and respective filament end.

3. The dental flosser unit according to claim 2, wherein said plastic bead is also preformed with a slit for accommodating the filament when the ferrule crimped to the end of the filament is received within said socket.

4. The dental flosser unit according to claim 2, wherein said plastic bead is constituted of two half-sections joined together by an integral hinge permitting the two half-sections to be opened and closed, each of said half-sections being formed with a recess, the recesses of the two half-sections together defining a socket for receiving the ferrule and the respective end of the filament when the two half-sections are closed.

5. The dental flosser unit according to claim 4, wherein each of said half-sections is further formed with a small recess communicating with its respective first-mentioned recess for accommodating the filament when the two half-sections are closed with the ferrule received in the socket defined by said first-mentioned recesses.

6. The dental flosser unit according to claim 4, wherein one of said two half-sections includes a pin, and the other includes a blind hole receiving said pin when the two half-sections are closed.

7. The dental flosser unit according to claim 1, wherein said plastic bead is molded over and embeds said ferrule.

8. The dental flosser unit according to claim 1, wherein said filament is of rectangular cross-section.

9. The dental flosser unit according to claim 1, wherein said filament includes at least one thread of high tensile strength having an outer covering of a low-friction material.

10. The dental flosser unit according to claim 9, wherein the filament includes a plurality of threads of high tensile strength covered by a low-friction material.

11. A dental flosser unit for flossing teeth, comprising:
 a filament having at least one thread of high tensile strength;
 a coating of low-friction material on said filament;
 and a plastic bead at each of the opposite ends of the filament penetrating through said coating of low-friction material and bonded directly to said at least one thread of high tensile strength.

12. The dental flosser unit according to claim 11, wherein said filament includes a plurality of threads each coated with said low-friction material and all bonded together by a wax.

13. A method of making a dental flosser unit, comprising:
 coating at least one thread of high tensile strength with a low-friction coating material having a melting point no higher than 280° C.;
 and injection molding a plastic bead at each of the opposite ends of the thread at a temperature of at least 280° C. to melt the coating of low-friction material and to bond the plastic bead directly to the high-tensile strength thread.

14. A dental flosser unit for flossing teeth including a filament of high tensile strength terminating in thickened end portions at its opposite ends; characterized in that each of said thickened end portions includes a bead made of a first part formed with a socket for receiving the respective filament end, and a second part formed with a plug of complementary configuration as said socket for insertion into the socket of the first part, thereby firmly clamping the respective filament end therein.

15. The dental flosser unit according to claim 14, wherein said socket in said first part, and said plug in said second part, are of complementary cylindrical configuration.

16. The dental flosser unit according to claim 14, wherein said first and second parts are of semi-spherical configuration.

17. The dental flosser unit according to claim 14, wherein said plug of the second part is secured in said socket of the first part by a friction fit.

18. The dental flosser unit according to claim 14, wherein said plug of the first part is secured in said socket of the second part by an adhesive.

19. The dental flosser unit according to claim 14, wherein said first and second parts are both of plastics material.

20. The dental flosser unit according to claim 14, wherein said first and second parts are both of metal.

* * * * *